United States Patent
Lautenschlaeger et al.

(10) Patent No.: US 12,178,624 B2
(45) Date of Patent: Dec. 31, 2024

(54) COMPUTED TOMOGRAPHY DEVICE WITH A RADIATION PROTECTION APPARATUS FOR COVERING OVER AN OPENING

(71) Applicant: Siemens Healthineers AG, Forchheim (DE)

(72) Inventors: Stefan Lautenschlaeger, Nuremberg (DE); Roman Achleitner, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 220 days.

(21) Appl. No.: 17/954,739

(22) Filed: Sep. 28, 2022

(65) Prior Publication Data

US 2023/0094501 A1  Mar. 30, 2023

(30) Foreign Application Priority Data

Sep. 30, 2021 (DE) .................. 20 2021 105 289.9

(51) Int. Cl.
*A61B 6/10* (2006.01)
*A61B 6/00* (2024.01)
*A61B 6/03* (2006.01)

(52) U.S. Cl.
CPC ............. *A61B 6/107* (2013.01); *A61B 6/032* (2013.01); *A61B 6/4435* (2013.01); *A61B 6/4405* (2013.01)

(58) Field of Classification Search
CPC ....... A61B 6/107; A61B 6/032; A61B 6/4435; A61B 6/4405; A61B 6/035
See application file for complete search history.

(56) References Cited

U.S. PATENT DOCUMENTS

| | | | |
|---|---|---|---|
| 8,057,097 B1 * | 11/2011 | Tybinkowski | A61B 6/4405 378/4 |
| 2009/0110152 A1 | 4/2009 | Manzke et al. | |
| 2013/0114788 A1 | 5/2013 | Crass | |
| 2021/0369214 A1 | 12/2021 | Korner | |

FOREIGN PATENT DOCUMENTS

| | | |
|---|---|---|
| DE | 102010025831 A1 | 1/2012 |
| DE | 102020206784 A1 | 7/2021 |

* cited by examiner

*Primary Examiner* — Courtney D Thomas
(74) *Attorney, Agent, or Firm* — Harness, Dickey & Pierce, P.L.C.

(57) ABSTRACT

A computed tomography device comprises: a gantry with an opening and a radiation protection apparatus configured to cover the opening, wherein the opening is configured to receive an examination object introduced into the opening along a system axis of the gantry; wherein the radiation protection apparatus has a radiation protection curtain, a curtain mounting and a pivot apparatus; wherein the curtain mounting has a bar-shaped area; wherein an upper edge of the radiation protection curtain is attached to the bar-shaped area such that the radiation protection curtain is stretched along the bar-shaped area and hangs down from the bar-shaped area; and wherein the curtain mounting is pivotably supported relative to the gantry about a pivot axis via the pivot apparatus.

18 Claims, 7 Drawing Sheets

COMPUTED TOMOGRAPHY DEVICE WITH A RADIATION PROTECTION APPARATUS FOR COVERING OVER AN OPENING

CROSS-REFERENCE TO RELATED APPLICATION(S)

The present application claims priority under 35 U.S.C. § 119 to German Patent Application No. 20 2021 105 289.9, filed Sep. 30, 2021, the entire contents of which are incorporated herein by reference.

FIELD

One or more example embodiments of the present invention relate to a computed tomography device (CT device) and/or to a method for radiation protection at a computed tomography device.

BACKGROUND

Mobile computed tomography devices are employed ever more in environments that were not originally set up for the operation of a device that emits ionizing scattered radiation. Examples of such environments are intensive care stations, operation and intervention rooms and mobile stroke units. In order to protect the environment of the computed tomography device from scattered radiation, pieces of cladding of the computed tomography device can have layers made of a radiation protection material, for example made of lead. Measures are further necessary to protect the environment of the computed tomography device against scattered radiation escaping from an opening of the computed tomography device on a front side or a rear side of a gantry of the computed tomography device.

U.S. Pat. No. 8,057,097 B1 discloses a radiation protection curtain, which is connected by a pivot to a scanner for covering over at least one side of the opening in the scanner during scanning.

DE 10 2020 206 784 A1 discloses a radiation protection apparatus with a radiation protection curtain and a radiation protection apparatus with a radiation protection body for covering over a tunnel-shaped opening of a gantry of a computed tomography device.

SUMMARY

An object of one or more example embodiments of the present invention is to make possible improved protection of an environment of a computed tomography device against scattered radiation that escapes from an opening of a gantry of the computed tomography device. At least the subject matter of each independent claim achieves this object. Further advantageous aspects are taken into consideration in the dependent claims.

One or more example embodiments of the present invention relate to a computed tomography device, having A gantry with an opening and a radiation protection apparatus for covering over the opening, wherein the opening is embodied in such a way that an examination object can be introduced along a system axis into the opening, Wherein the radiation protection apparatus has a radiation protection curtain, a curtain mounting and a pivot apparatus, Wherein the curtain mounting has a bar-shaped area, wherein an upper edge of the radiation protection curtain is fastened to the bar-shaped area in such a way that the radiation protection curtain is stretched out along the bar-shaped area and hangs down from the bar-shaped area, Wherein the curtain mounting is supported pivoted by the pivot apparatus in such a way relative to the gantry about a pivot axis that, by a first pivoting movement of the curtain mounting about the pivot axis, the curtain mounting can be moved relative to the gantry from a first position to a second position, Wherein the radiation protection curtain covers over a side surface of the gantry and does not cover the opening when the curtain mounting is located in the first position relative to the gantry, Wherein the radiation protection curtain covers over the opening when the curtain mounting is located in the second position relative to the gantry.

The bar-shaped area can in particular be embodied in such a way that it can be gripped from above with one hand by a person operating the computed tomography device, for example in the overhead grip or in the pliers grip in order to pivot the curtain mounting manually about the pivot axis. This makes possible an especially ergonomic operation of the radiation protection apparatus. The bar-shaped area can be embodied in the form a rail for example. The radiation protection curtain can for example be supported relative to the rail for movement along the rail.

With the aid of the radiation protection curtain for example, gaps that are located between the cladding of the gantry on the one hand and the patient and/or the patient bed on the other hand can be covered over. The radiation protection curtain can in particular have a flexible planar radiation protection material and/or essentially be impermeable for scattered radiation of the ionizing radiation used in the computed tomography device for examination of the examination object. The flexible planar radiation protection material can be free from lead or can contain lead for example.

Cables and/or tubes connected to the patient, in particular breathing tubes, can be arranged in such a way that the radiation protection curtain first touches the body of the patient during the first pivoting movement and only touches the cables and/or tubes connected to the patient when a significant part of the radiation protection curtain already rests flat against the body of the patient. What can be achieved by this is that as little weight as possible of the radiation protection curtain is loaded onto the cables and/or tubes connected to the patient. This reduces the danger of the cables and/or tubes connected to the patient being torn by the radiation protection curtain and damaged.

In particular there can be provision for the curtain mounting to be pivotably supported about a pivot axis via the pivot apparatus relative to the gantry in such a way that through a second pivoting movement the curtain mounting can be moved about the pivot axis relative to the gantry from the second position to the second position.

There can furthermore be provision for the radiation protection apparatus to further have a pivot drive for driving the first pivoting movement and/or for driving the second pivoting movement. The pivot drive can for example be configured to exert a turning moment on the curtain mounting with regard to the pivot axis, which pivots the curtain mounting to the second position.

In particular there can be provision for the radiation protection curtain not to cover the side surface of the gantry when the curtain mounting is located in the second position relative to the gantry.

In particular there can be provision for the gantry to have an inner area and cladding for delimiting the inner area from an environment. The side surface of the gantry can in particular be a side surface of the cladding of the gantry.

One form of embodiment makes provision for the side surface of the gantry to be essentially parallel and/or coaxial to the system axis. One form of embodiment makes provision for the system axis to be essentially horizontal and/or for the pivot axis to be essentially vertical.

For example the side surface of the gantry can be curved about an axis of curvature parallel to the system axis and/or extend in a side plane parallel to the system axis. One form of embodiment makes provision for the system axis to be essentially horizontal, in particular horizontal and for the pivot axis to be essentially vertical, in particular vertical. One form of embodiment makes provision for the bar-shaped area to be located above the opening.

One form of embodiment makes provision for the bar-shaped area to be essentially straight. One form of embodiment makes provision for the bar-shaped area to be essentially parallel to the system axis when the curtain mounting is located in the first position relative to the gantry, and/or for the bar-shaped area to be essentially at right angles to the system axis when the curtain mounting is located in the second position relative to the gantry.

One form of embodiment makes provision for the curtain mounting to have a pivot arm area, wherein the bar-shaped area is spaced away from the pivot axis in a pivot arm direction via the pivot arm area. Furthermore there can be provision for the pivot arm direction to be essentially at right angles to the system axis when the curtain mounting is located in the first position relative to the gantry, and/or for the pivot arm direction to be essentially parallel to the system axis when the curtain mounting is located in the second position relative to the gantry.

The pivot arm direction can for example be essentially at right angles to the bar-shaped area, in particular at right angles.

In particular there can be provision for the bar-shaped area to lie in a reference plane, which is able to be defined relative to the bar-shaped area, which is parallel to the pivot axis and is spaced away from the pivot axis. Furthermore there can be provision for the radiation protection curtain to extend flat in the reference plane when the curtain mounting is located in the second position relative to the gantry and the radiation protection curtain is hanging down freely from the bar-shaped area.

Furthermore there can be provision for a front side of the cladding of the gantry to extend flat in a frontal plane of the gantry, wherein the front side of the cladding of the gantry surrounds a front side of the opening in an annular shape. The frontal plane of the gantry can for example be essentially at right angles to the system axis, in particular at right angles. Furthermore there can be provision for the reference plane to be essentially parallel, in particular parallel, to the frontal plane when the curtain mounting is located in the second position relative to the gantry. The reference plane can be vertical for example. The frontal plane can be vertical for example.

In particular there can be provision for the gantry and the pivot axis to be located in the same half space with regard to the frontal plane. In particular there can be provision for the curtain mounting to be configured in such a way that the gantry and the bar-shaped area are located in the same half space with regard to the frontal plane when the curtain mounting is located in the first position relative to the gantry and/or for the gantry and the bar-shaped area to be located in different half spaces with regard to the frontal plane when the curtain mounting is located in the second position relative to the gantry. For example the pivot arm area can protrude through the frontal plane when the curtain mounting is located in the second position relative to the gantry.

Furthermore there can be provision for the curtain mounting to have an axial area, wherein the bar-shaped area is spaced away from the gantry via the axial area along the pivot axis 7A. Despite a curved cladding of the gantry, this enables a sufficient freedom of movement for pivoting movements of the curtain mounting about the pivot axis to be made possible.

One form of embodiment makes provision for an angle width of the first pivoting movement of the curtain mounting about the pivot axis to be greater than 250 degrees, in particular greater than 260 degrees, and/or less than 290 degrees, in particular less than 280 degrees. The angle width of the first pivoting movement of the curtain mounting about the pivot axis can for example essentially be 270 degrees, in particular it can be 270 degrees.

One form of embodiment makes provision for the radiation protection curtain to have a first surface, wherein the first surface is facing away from the gantry when the curtain mounting is located in the first position relative to the gantry, wherein the first surface is facing towards the gantry when the curtain mounting is located in the second position relative to the gantry. In particular there can be provision for the radiation protection curtain to have a second surface, for the second surface to be facing away from the gantry when the curtain mounting is located in the second position relative to the gantry and to be facing towards the second surface of the gantry when the curtain mounting is located in the first position relative to the gantry.

The first surface can in particular be facing towards an examination object when the examination object is introduced into the opening and the curtain mounting is located in the second position relative to the gantry. The radiation protection curtain can in particular rest flat against the side surface of the gantry when the curtain mounting is located in the first position relative to the gantry. When the curtain mounting is located in the first position relative to the gantry, a thorough cleaning of the first surface is possible in a simple manner. Thus it is not necessary to make it possible easily to remove the radiation protection curtain for cleaning. Therefore mechanical connections for holding the radiation protection curtain can be configured with increased security in order to exclude the possibility of the radiation protection curtain falling down onto the patient.

One form of embodiment makes provision for the curtain mounting to have a telescopic bar, wherein the telescopic bar forms the bar-shaped area.

The telescopic bar can be embodied in particular in the form of a telescopic rail. In particular there can be provision for a length of the bar-shaped area to be set by changing the length of the telescopic bar. For example the bar-shaped area can be shortened by collapsing the telescopic bar in order to reduce the need for space around the pivot axis for the first pivoting movement and/or for the second pivoting movement and/or for reducing the need for space along the system axis for a transport movement of the gantry, which occurs at right angles to the system axis when the curtain mounting is located in the first position relative to the gantry. This is advantageous in particular in situations where space is tight, as is often encountered in intensive-care stations.

For example the bar-shaped area can be lengthened by pulling apart the telescopic bar, for example for an enlargement of an effective coverage surface of the radiation protection curtain, when the curtain mounting is located in the second position relative to the gantry.

One form of embodiment makes provision for the radiation protection curtain to have a first part curtain and a second part curtain, which are supported displaceably relative to one another along the bar-shaped area.

This enables an effective coverage surface of the radiation protection curtain to be changed with regard to its size and/or its shape. If need be simple access by an operator to the examination object by opening the gap can be made possible when the examination object is introduced into the opening and the curtain mounting is located in the second position relative to the gantry.

For example there can be provision for the first part curtain to be able to be displaced along the entire length of the bar-shaped area. For example there can be provision for the second part curtain to be able to be displaced along the entire length of the bar-shaped area. For example there can be provision for the telescopic bar to have a first segment and a second segment, for the first part curtain to be attached to the first segment and for the second part curtain to be attached to the second segment, wherein the second segment is supported telescopically displaceable relative to the first segment.

One form of embodiment makes provision for the radiation protection curtain to have a part curtain connection unit, which is configured, in an area in which the first part curtain and the second part curtain overlap with one another when closing a gap that is located between the first part curtain and the second part curtain, to connect the first part curtain and the second part curtain releasably to one another and thus to counteract the gap being opened.

The part curtain connection unit can be configured for example to form a magnetic connection between the first part curtain and the second part curtain. The first part curtain can for example have a first connecting element of the part curtain connection unit. The second part curtain can for example have a second connecting element of the part curtain connection unit, which is arranged corresponding to the first connecting element of the part curtain connection unit. The first connecting element of the part curtain connection unit can for example be a magnet or a ferromagnetic area. The second connecting element of the part curtain connection unit can for example be a magnet or a ferromagnetic area when the first connecting element is a magnet. The second connecting element of the part curtain connection unit can for example be a magnet when the first connecting element of the part curtain connection unit is a ferromagnetic area. Magnetic connections can be realized with contact surfaces that are particularly easy to clean. Basically it would also be possible to realize the part curtain connection unit in the form of a Velcro connection.

One form of embodiment makes provision for the radiation protection curtain to have a first side flap, which is able to be folded over relative to a first central area of the radiation protection curtain at a first edge of the radiation protection curtain, wherein the first edge of the radiation protection curtain is essentially at right angles to the bar-shaped area.

Furthermore there can be provision for the radiation protection curtain to have a second side flap, which is able to be folded over relative to a second central area of the radiation protection curtain at a second edge of the radiation protection curtain, wherein the second edge of the radiation protection curtain is essentially at right angles to the bar-shaped area. The first central area can for example be the first part curtain. The second central area can for example be the second part curtain.

The first side flap can in particular be folded over in such a way that a first side flap plane, in which the first side flap extends flat, is essentially vertical, in particular vertical and/or is essentially at right angles to the bar-shaped area, in particular at right angles to it. The second side flap can in particular be folded over in such a way that a second side flap plane, in which the second side flap extends flat, is essentially vertical, in particular vertical and/or is essentially at right angles to the bar-shaped area, in particular at right angles to it. Thus the coverage of the opening in particular with regard to that scattered radiation that escapes from the opening to the left or right side of the gantry, is improved.

One form of embodiment makes provision for the radiation protection curtain to have a first side flap connection unit, which is configured, in a state of the radiation protection curtain in which the first side flap rests flat against the first central area of the radiation protection curtain, to connect the first side flap and the first central area of the radiation protection curtain releasably to one another and thus to counteract a folding up of the first side flap relative to the first central area of the radiation protection curtain about the first edge of the radiation protection curtain.

Furthermore there can be provision for the radiation protection curtain to have a second side flap connection unit, which is configured in a state of the radiation protection curtain in which the second side flap rests flat against the second central area of the radiation protection curtain, to connect the second side flap and the second central area of the radiation protection curtain releasably to one another and thus to counteract a folding up of the second side flap relative to the second central area of the radiation protection curtain about the second edge of the radiation protection curtain.

The first side flap connection unit can be configured for example to form a magnetic connection between the first side flap and the first central area of the radiation protection curtain. The first side flap can for example have a first connecting element of the first side flap connection unit. The first central area of the radiation protection curtain can for example have a second connecting element of the first side flap connection unit, which is arranged corresponding to the first connecting element of the first side flap connection unit.

The first connecting element of the first side flap connection unit can for example be a magnet or a ferromagnetic area. The second connecting element of the first side flap connection unit can for example be a magnet or a ferromagnetic area when the first connecting element of the first side flap connection unit is a magnet. The second connecting element of the first side flap connection unit can for example be a magnet when the first connecting element of the first side flap connection unit is a ferromagnetic area. Magnetic connections can be realized with contact surfaces that are especially easy to clean. Basically it would also be possible to realize the first side flap connection unit in the form of a Velcro connection.

The second side flap connection unit can for example be configured to form a magnetic connection between the second side flap and the second central area of the radiation protection curtain. The second side flap can for example have a first connecting element of the second side flap connection unit. The second central area of the radiation protection curtain can for example have a second connecting element of the second side flap connection unit, which is arranged corresponding to the first connecting element of the second side flap connection unit.

The first connecting element of the second side flap connection unit can for example be a magnet or a ferromagnetic area. The second connecting element of the second side flap connection unit can for example be a magnet or a ferromagnetic area when the first connecting element of the second side flap connection unit is a magnet. The second connecting element of the first side flap connection unit can for example be a magnet when the first connecting element of the second side flap connection unit is a ferromagnetic area. Magnetic connections can be realized with contact surfaces that are especially easy to clean. Basically it would also be possible to realize the second side flap connection unit in the form of a Velcro connection.

One form of embodiment makes provision for the radiation protection curtain to have an area transparent for visible light, so that the examination object is able to be seen through the radiation protection curtain when the examination object is located in the opening and when the curtain mounting is located in the second position relative to the gantry, so that the radiation protection curtain covers over the opening.

The area transparent for visible light can be embodied for example in the form of a lead glass window. The transparent area can for example be framed by the flexible planar radiation protection material of the radiation protection curtain or be arranged between the bar-shaped area and the flexible planar radiation protection material of the radiation protection curtain in such a way that it forms the upper edge of the radiation protection curtain. In this way the observation of the patient and because of the incident light also the wellbeing of the patient can be enhanced, in particular when the radiation protection curtain is covering over the opening. Further a sufficient incidence of light into the opening can be made possible by this when the rear side of the opening is closed off by a radiation protection element impermeable for visible light.

The area transparent for visible light can for example be embodied rectangular or round and/or be arranged for example in an upper section of the radiation protection curtain in such a way that an operator standing at a front side of the gantry can look from above at the examination object through the area transparent for visible light when the examination object is introduced into the opening and the curtain mounting is located in the second position relative to the gantry.

One form of embodiment makes provision for the gantry to have a first gantry part and a second gantry part, wherein the first gantry part has a rotatably supported rotor with a projection data acquisition system, wherein the second gantry part has at least one section of the opening, wherein the curtain mounting is connected via the pivot apparatus to the second gantry part and is supported pivotably about the pivot axis relative to the second gantry part. The projection data acquisition system can for example have an x-ray source and an x-ray detector, which interoperates with the x-ray source.

In this case the first gantry part can be supported for movement relative to the second gantry part in such a way that a translation movement, in particular a translation movement along the system axis, of the first gantry part relative to the second gantry part can be carried out, while at the same time the second gantry part stays still relative to the examination object and the radiation protection apparatus stays still relative to the examination object and relative to the at least one section of the opening when the examination object is located in the opening. This enables a computed tomography scan of the examination object to be carried out while the radiation protection apparatus stays still relative to the examination object. On the one hand this makes a gapless coverage of the opening during the computed tomography scan easier. On the other hand the danger that cables and/or tubes connected to the patient will be damaged in this case because of a movement of the radiation protection apparatus is reduced.

One form of embodiment makes provision for the first gantry part to have a rotating support and a carrier structure, wherein the rotor is connected via the rotating support to the carrier structure and is supported rotatably about the system axis relative to the carrier structure.

The examination object can for example be a part of the body of a patient, in particular a head of a patient. The computed tomography device can in particular be embodied as a head computed tomography device and/or as a mobile computed tomography device. The patient can for example involve a human being, in particular a baby, or an animal. A longitudinal axis of the patient can for example be parallel, in particular identical, or skewed relative to the system axis or intersect with the system axis.

The examination object can for example be an object, in particular a phantom for calibration of the computed tomography device.

One or more example embodiments of the present invention further relate to a method for radiation protection at a computed tomography device, wherein the computed tomography device has a gantry with an opening and a radiation protection apparatus for covering over the opening, wherein the radiation protection apparatus has a radiation protection curtain, a curtain mounting and a pivot apparatus, wherein the curtain mounting has a bar-shaped area, wherein an upper edge of the radiation protection curtain is attached to the bar-shaped area in such a way that the radiation protection curtain is stretched along the bar-shaped area and hangs down from the bar-shaped area, wherein the curtain mounting is pivotably supported via the pivot apparatus relative to the gantry about a pivot axis, the method comprising:

An arrangement of the curtain mounting in a first position relative to the gantry, wherein the radiation protection curtain covers over a side surface of the gantry and does not cover the opening when the curtain mounting is located in the first position relative to the gantry, An introduction of an examination object along a system axis of the gantry into the opening, A movement of the curtain mounting through a first pivoting movement of the curtain mounting about the pivot axis relative to the gantry from the first position to a second position, wherein the radiation protection curtain covers over the opening when the curtain mounting is located in the second position relative to the gantry.

The method for radiation protection can be carried out in particular on the inventive computed tomography device.

Within the framework of the present invention, features that are described with regard to different forms of embodiments of the present invention and/or different claim categories (method, use, apparatus, system, arrangement etc.) can be combined to form further forms of embodiments of the present invention. For example a claim that relates to an apparatus can also be further developed with features that are described or claimed in conjunction with a method and vice versa. Functional features of a method in this case can be carried by correspondingly embodied physical components. The use of the indefinite article "a" or "an" does not exclude the features concerned also being able to be present more than once. The use of the formulation "essentially" before a characteristic, for example before "parallel", "at right angles" or "straight" does not exclude this characteristic applying exactly.

BRIEF DESCRIPTION OF THE DRAWINGS

The present invention will be explained below with the aid of exemplary embodiments that refer to the enclosed figures. The representation in the figures is schematic, greatly simplified and not absolutely true-to-scale.

DETAILED DESCRIPTION

Figure 1:
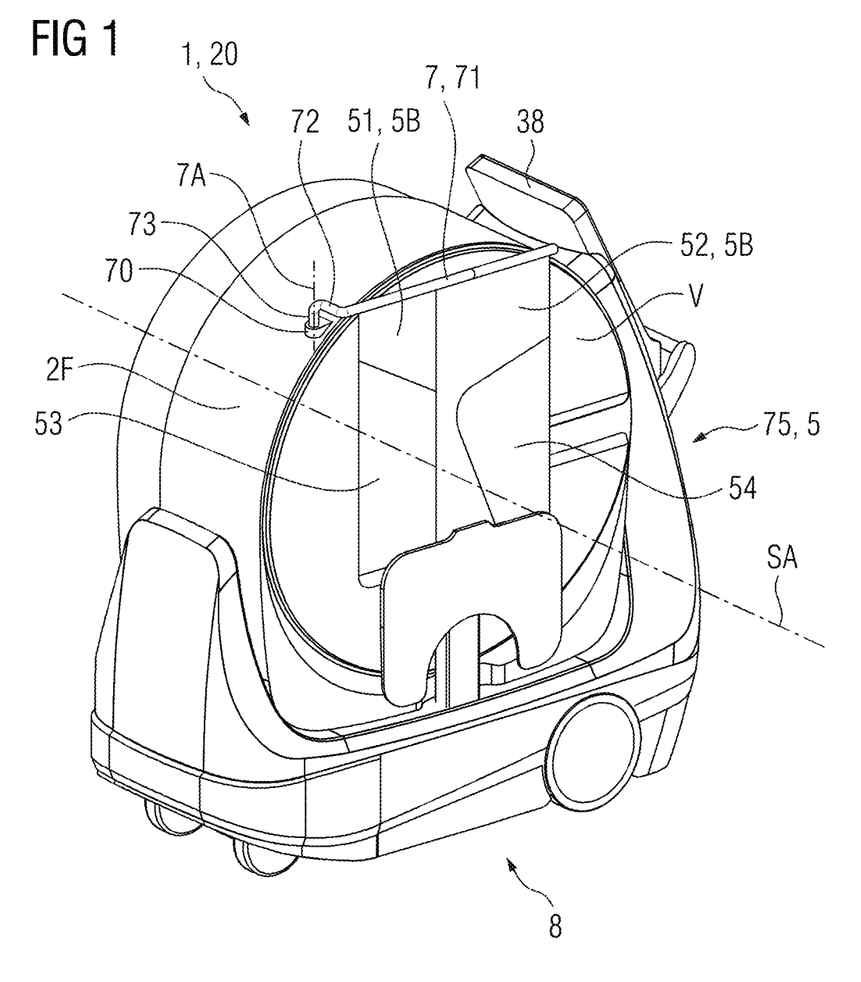
FIGS. 1 to 8 show a computed tomography device with a radiation protection apparatus for covering over an opening.

FIG. 1 shows the computed tomography device 1, having
A gantry 20 with an opening 9 and a radiation protection apparatus 75 for covering over the opening 9, wherein the opening 9 is embodied in such a way that an examination object 14 can be introduced along a system axis SA of the gantry 20 into the opening 9,
Wherein the radiation protection apparatus 75 has a radiation protection curtain 5, a curtain mounting 7 and a pivot apparatus 70,
Wherein the curtain mounting 7 has a bar-shaped area 71, wherein an upper edge of the radiation protection curtain 5 is attached to the bar-shaped area 71 in such a way that the radiation protection curtain 5 is stretched along the bar-shaped area 71 and hangs down from the bar-shaped area 71,
Wherein the curtain mounting 7 is supported pivotably about a pivot axis 7A via the pivot apparatus 70 in such a way relative to the gantry 20 that, through a first pivoting movement of the curtain mounting 7 about the pivot axis 7A, the curtain mounting 7 can be moved relative to the gantry 20 from a first position to a second position,
Wherein the radiation protection curtain 5 covers over a side surface 2F of the gantry 20 and does not cover the opening 9 when the curtain mounting 7 is located in the first position relative to the gantry 20,
Wherein the radiation protection curtain 5 covers over the opening 9 when the curtain mounting 7 is located in the second position relative to the gantry 20.

In the state of the radiation protection apparatus 75 shown in FIG. 1 the curtain mounting 7 is located in the second position.

The side surface 2F of the gantry 20 is essentially parallel and coaxial to the system axis SA. The system axis SA is essentially horizontal, the pivot axis 7A is essentially vertical. The bar-shaped area 71 is essentially straight. The bar-shaped area 71 is essentially parallel to the system axis SA when the curtain mounting 7 is located in the first position relative to the gantry 20. The bar-shaped area 71 is essentially at right angles to the system axis SA when the curtain mounting 7 is located in the second position relative to the gantry 20.

The curtain mounting 7 has a pivot arm area 72, wherein the bar-shaped area 71 is spaced away from the pivot axis 7A along a pivot arm direction 7B via the pivot arm area 72, wherein the pivot arm direction 7B is essentially at right angles to the system axis SA when the curtain mounting 7 is located in the first position relative to the gantry 20, wherein the pivot arm direction 7B is essentially parallel to the system axis SA when the curtain mounting 7 is located in the second position relative to the gantry 20.

The radiation protection curtain 5 has a first part curtain 51 and a second part curtain 52, which are supported displaceably relative to one another along the bar-shaped area 71.

The gantry 20 has the drive mechanism 8 for a transport movement of the gantry 20, wherein the transport movement is made at right angles to the system axis SA. The gantry 20 has a touch-sensitive screen 38 for operation of the computed tomography device 1.

The curtain mounting 7 has an axial area 73, wherein the bar-shaped area 71 is spaced away from the gantry 20 along the pivot axis 7A via the axial area 73. The curtain mounting 7 has a telescopic bar, wherein the telescopic bar forms the bar-shaped area 71.

Figure 2:
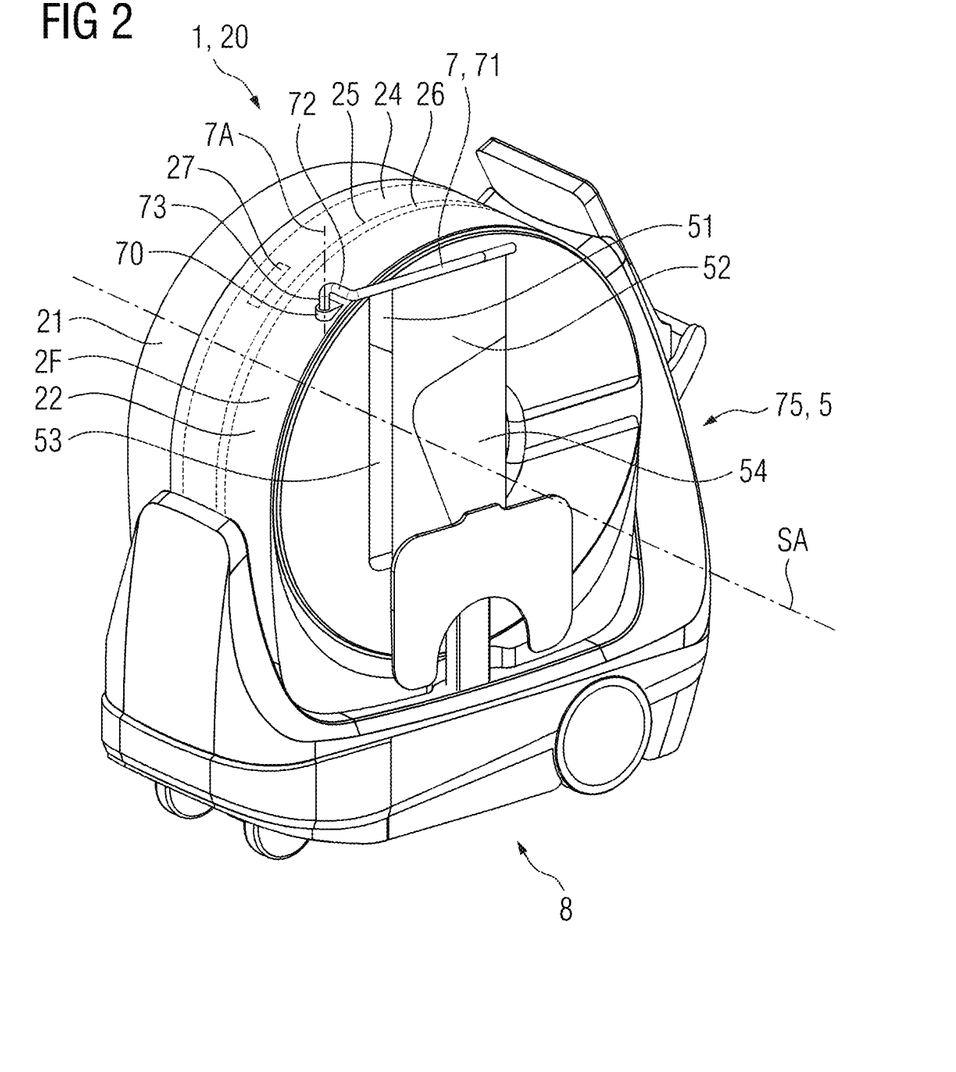

FIG. 2 shows the computed tomography device 1, wherein, because the telescopic bar is pushed together, the length of the bar-shaped area 71 is shortened compared to the state of the radiation protection apparatus 75 shown in FIG. 1.

The gantry 20 has a first gantry part 21 and a second gantry part 22, wherein the first gantry part 21 has a rotatably supported rotor 24 with a projection data acquisition system 27, wherein the second gantry part 22 has at least one section of the opening 9, wherein the curtain mounting 7 is connected via the pivot apparatus 70 to the second gantry part 22 and is supported pivotably relative to the second gantry part 22 about the pivot axis 7A.

The first gantry part 21 is supported movably relative to the second gantry part 22 in such a way that a translation movement of the first gantry part 21 relative to the second gantry part 22 can be carried out while at the same time the second gantry part 22 stays still relative to the examination object 14 and the radiation protection apparatus 75 stays still relative to the examination object 14 and relative to the at least one section of the opening 9 when the examination object 14 is located in the opening 9.

The first gantry part 21 has a rotating support 25 and a carrier structure 26, wherein the rotor 24 is connected via the rotating support 25 to the carrier structure 26 and is supported rotatably about the system axis SA relative to the carrier structure 26.

Figure 3:
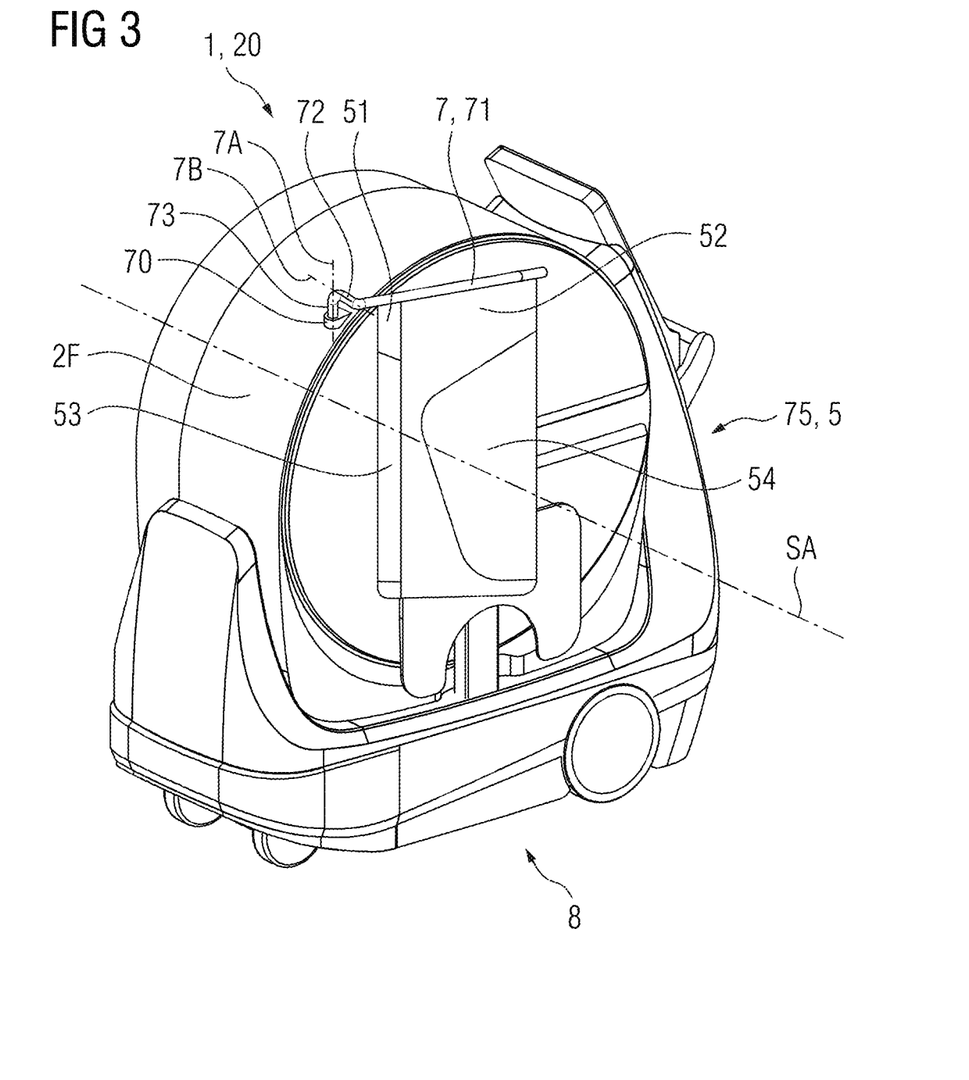

FIG. 3 shows the computed tomography device 1, wherein the curtain mounting 7 is located in an intermediate position between the first position and the second position.

Figure 4:
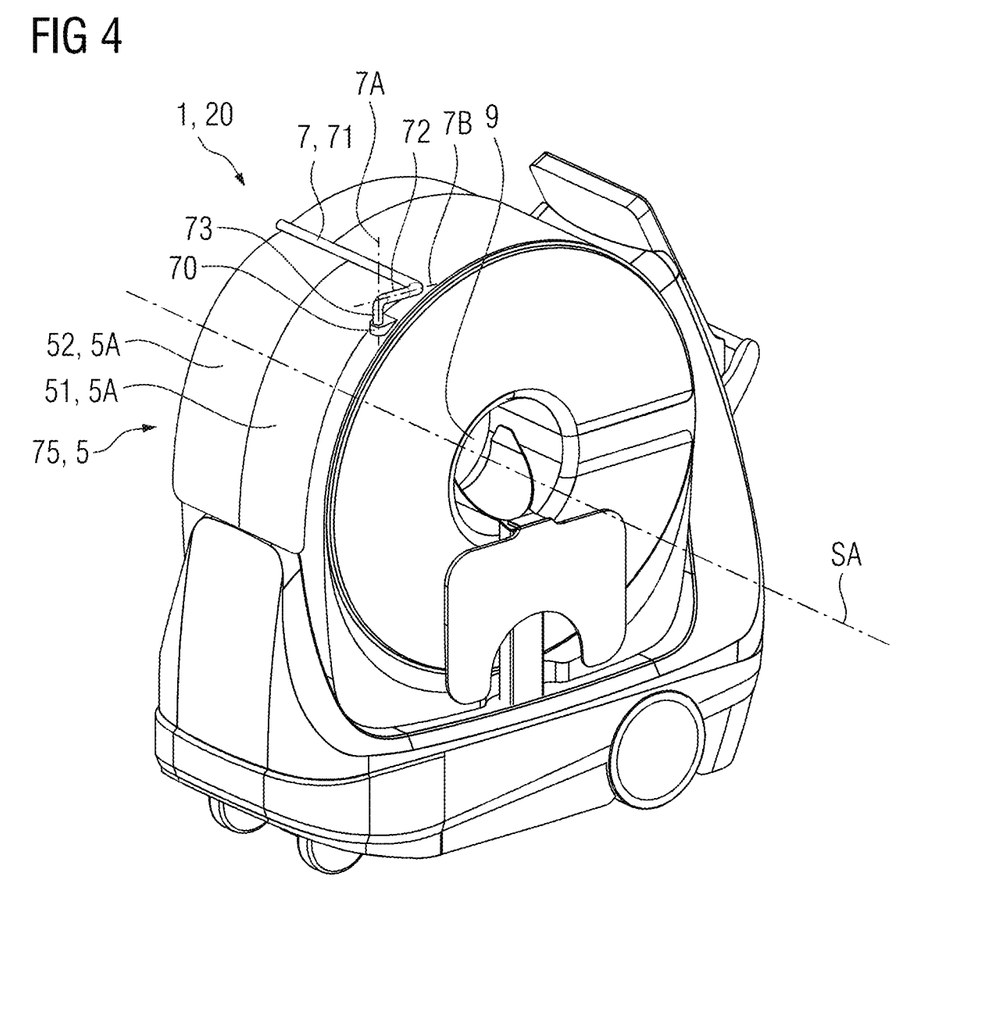
Figure 5:
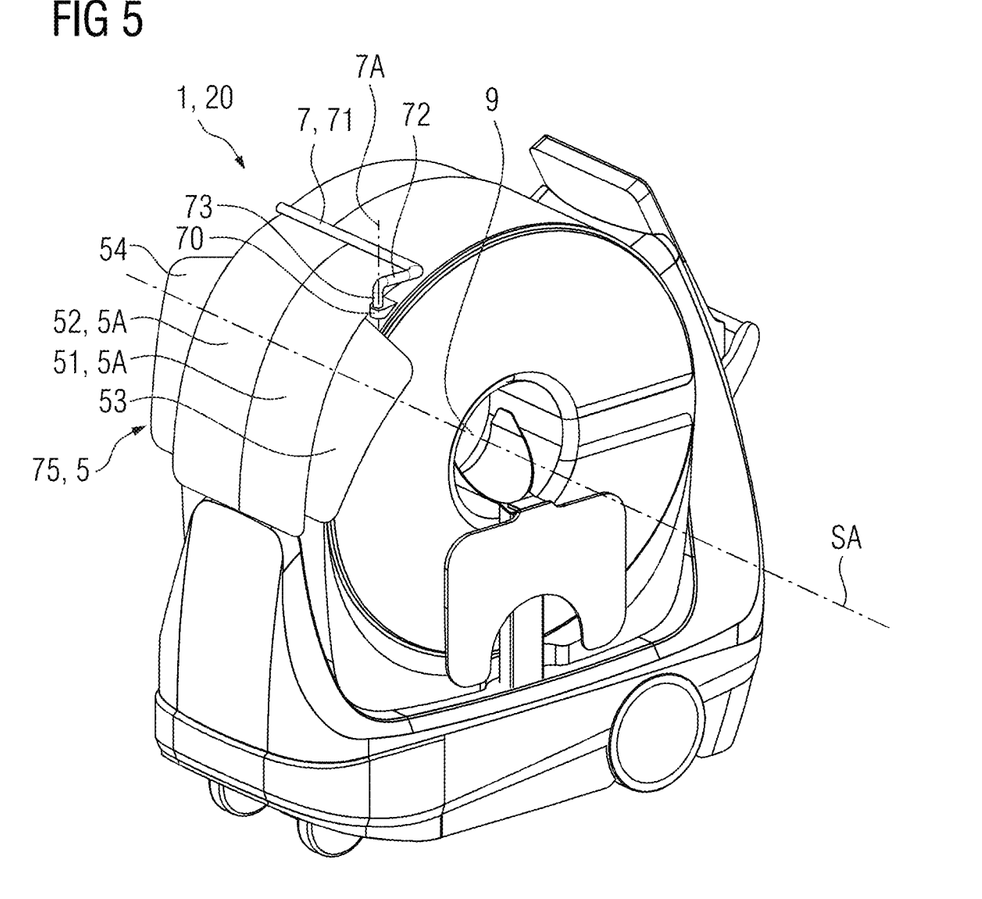

FIG. 4 shows the computed tomography device 1, wherein the curtain mounting 7 is located in the first position. The radiation protection curtain 5 has a first surface 5A, wherein the first surface 5A is facing away from the gantry 20 when the curtain mounting 7 is located in the first position relative to the gantry 20, wherein the first surface 5A is facing towards the gantry 20 when the curtain mounting 7 is located in the second position relative to the gantry 20. The radiation protection curtain 5 has a second surface 5B, wherein the second surface 5B is facing away from the gantry 20 when the curtain mounting 7 is located in the second position relative to the gantry 20, wherein the second surface 5B is facing towards the gantry 20 when the curtain mounting 7 is located in the first position relative to the gantry 20.

Figure 6:
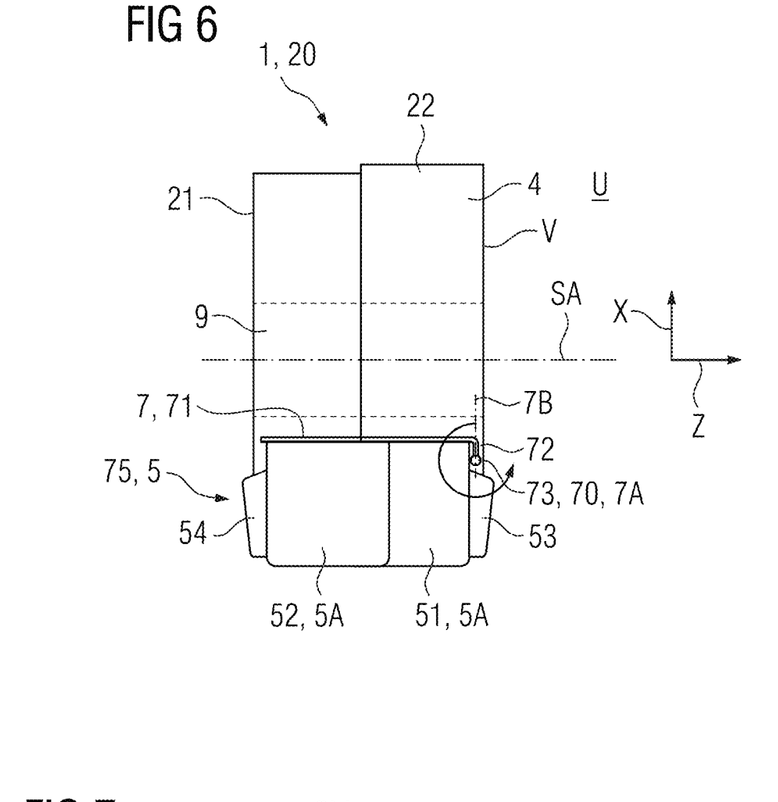

FIG. 6 shows the computed tomography device 1, wherein the curtain mounting 7 is located in the first position. The first pivoting movement is indicated in FIG. 6 by the curved arrow. An angle width of the first pivoting movement of the curtain mounting 7 about the pivot axis 7A is greater than 250 degrees and less than 290 degrees. The gantry 20 has an inner area 4 and cladding V for delimiting the inner area 4 from an environment U. The X direction X is horizontal and at right angles to the system axis SA. The Y direction Y is vertical. The Z direction Z is horizontal and parallel to the system axis SA.

Figure 7:
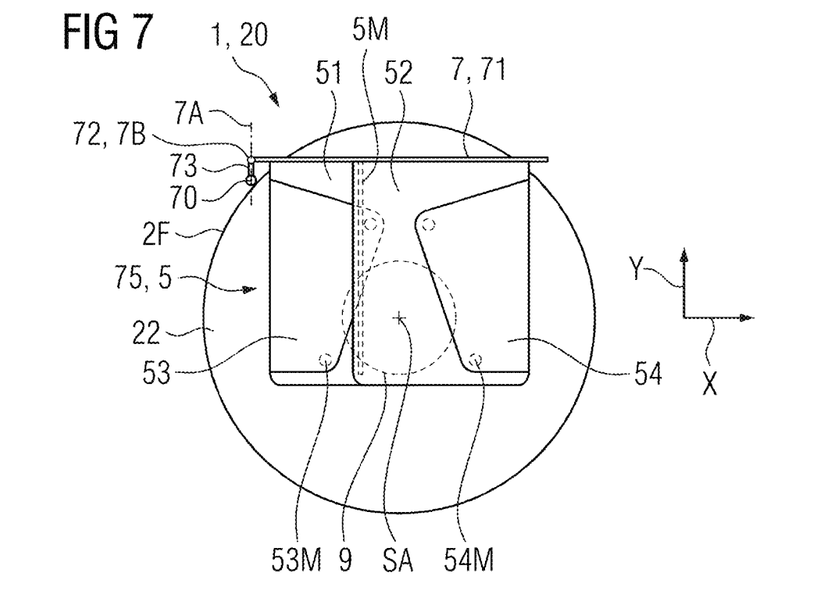

FIG. 7 shows the computed tomography device 1, wherein the curtain mounting 7 is located in the second position. The radiation protection curtain 5 has a part curtain connection unit 5M, which is configured, in an area in which the first part curtain 51 and the second part curtain 52 overlap one another while closing off a gap that is located between the first part curtain 51 and the second part curtain 52, to connect the first part curtain 51 and the second part curtain 52 releasably to one another and thus to counteract an opening of the gap. The part curtain connection unit 5M is embodied in the form of a strip, for example a magnetic strip.

The radiation protection curtain 5 has a first side flap 53, which is able to be folded relative to a first central area of the radiation protection curtain 5 about a first edge of the radiation protection curtain 5, wherein the first edge of the radiation protection curtain 5 is essentially at right angles to the bar-shaped area 71.

The radiation protection curtain 5 has a second side flap 54, which is able to be folded relative to a second central area of the radiation protection curtain 5 about a second edge of the radiation protection curtain 5, wherein the second edge of the radiation protection curtain 5 is essentially at right angles to the bar-shaped area 71. In the example shown the first central area is the first part curtain 51. In the example shown the second central area is the second part curtain 52.

The radiation protection curtain 5 has a first side flap connection unit 53M, which is configured, in a state of the radiation protection curtain 5 in which the first side flap 53 rests flat against the first central area of the radiation protection curtain 5, to connect the first side flap 53 and the first central area of the radiation protection curtain 5 releasably to one another and thus to counteract a folding up of the first side flap 53 relative to the first central area of the radiation protection curtain 5 about the first edge of the radiation protection curtain 5.

The radiation protection curtain 5 has a second side flap connection unit 54M, which is configured, in a state of the radiation protection curtain 5 in which the second side flap 54 rests flat against the second central area of the radiation protection curtain 5, to connect the second side flap 54 and the second central area of the radiation protection curtain 5 releasably to one another and thus to counteract a folding up of the second side flap 54 relative to the second central area of the radiation protection curtain 5 about the second edge of the radiation protection curtain 5.

The radiation protection curtain 5 can have an area transparent for visible light, so that the examination object 14 can be seen through the radiation protection curtain 5 when the examination object 14 is located in the opening 9 and when the curtain mounting 7 is located in the second position relative to the gantry 20, so that the radiation protection curtain 5 covers over the opening 9.

Figure 8:
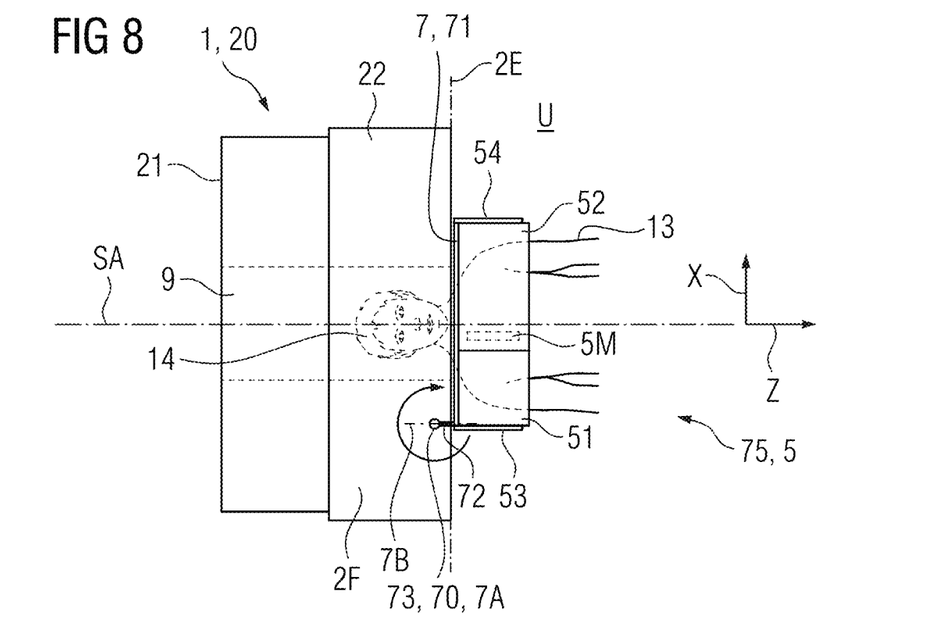

FIG. 8 shows the computed tomography device 1, wherein the curtain mounting 7 is located in the second position. The second pivoting movement is indicated in FIG. 8 by the curved arrow. A front side of the cladding V of the gantry 20 extends flat in a frontal plane 2E of the gantry 20, wherein the front side of the cladding V of the gantry 20 surrounds a front side of the opening 9 in a ring shape. The frontal plane 2E of the gantry 20 is at right angles to the system axis SA.

The examination object 14 is the head of the patient 13. The computed tomography device 1 is a mobile head computed tomography device. The computed tomography device 1 further has a headrest in which the head of the patient 13 can be accommodated, and an upper body support plate on which the upper body of the patient 13 can be supported. This is adjoined in the Z direction by a patient bed for support of the patient 13.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A computed tomography device, comprising:
   a gantry having an opening and a radiation protection apparatus configured to cover the opening,
   wherein the opening is configured to receive an examination object introduced into the opening along a system axis of the gantry,
   wherein the radiation protection apparatus includes a radiation protection curtain, a curtain mounting and a pivot apparatus,
   wherein the curtain mounting has a bar-shaped area,
   wherein an upper edge of the radiation protection curtain is attached to the bar-shaped area such that the radiation protection curtain is stretched along the bar-shaped area and hangs down from the bar-shaped area,
   wherein, via the pivot apparatus, the curtain mounting is pivotably supported relative to the gantry about a pivot axis such that, through a first pivoting movement of the curtain mounting about the pivot axis, the curtain mounting is configured to move relative to the gantry from a first position to a second position,
   wherein the radiation protection curtain is configured to cover a side surface of the gantry and to not cover the opening when the curtain mounting is in the first position,
   wherein the radiation protection curtain is configured to cover the opening when the curtain mounting is in the second position,
   wherein the radiation protection curtain has a first side flap configured to be folded relative to a first central area of the radiation protection curtain about a first edge of the radiation protection curtain, and
   wherein the first edge of the radiation protection curtain is substantially perpendicular to the bar-shaped area.

2. The computed tomography device as claimed in claim 1, wherein the side surface of the gantry is at least one of substantially parallel or substantially coaxial to the system axis.

3. The computed tomography device as claimed in claim 1,
   wherein the system axis is substantially horizontal, and
   wherein the pivot axis is substantially vertical.

4. The computed tomography device as claimed in claim 1, wherein the bar-shaped area is substantially straight.

5. The computed tomography device as claimed in claim 1,
   wherein the bar-shaped area is substantially parallel to the system axis when the curtain mounting is in the first position, and
   wherein the bar-shaped area is substantially perpendicular to the system axis when the curtain mounting is in the second position.

6. The computed tomography device as claimed in claim 5,
   wherein the curtain mounting has a pivot arm area,
   wherein the bar-shaped area is spaced apart from the pivot axis along a pivot arm direction via the pivot arm area,
   wherein the pivot arm direction is substantially perpendicular to the system axis when the curtain mounting is in the first position, and
   wherein the pivot arm direction is substantially parallel to the system axis when the curtain mounting is in the second position.

7. The computed tomography device as claimed in claim 1,
wherein the curtain mounting has a pivot arm area,
wherein the bar-shaped area is spaced apart from the pivot axis along a pivot arm direction via the pivot arm area,
wherein the pivot arm direction is substantially perpendicular to the system axis when the curtain mounting is in the first position, and
wherein the pivot arm direction is substantially parallel to the system axis when the curtain mounting is in the second position.

8. The computed tomography device as claimed in claim 1,
wherein an angle width of the first pivoting movement of the curtain mounting about the pivot axis is greater than 250 degrees and less than 290 degrees.

9. The computed tomography device as claimed in claim 1,
wherein the radiation protection curtain has a first surface,
wherein the first surface faces away from the gantry when the curtain mounting is in the first position, and
wherein the first surface faces the gantry when the curtain mounting is in the second position.

10. The computed tomography device as claimed in claim 9,
wherein the curtain mounting has a telescopic bar, and
wherein the telescopic bar forms the bar-shaped area.

11. The computed tomography device as claimed in claim 9,
wherein the radiation protection curtain has a first curtain part and a second curtain part, the first curtain part and the second curtain part being supported displaceably relative to one another along the bar-shaped area.

12. The computed tomography device as claimed in claim 1,
wherein the curtain mounting has a telescopic bar, and
wherein the telescopic bar forms the bar-shaped area.

13. The computed tomography device as claimed in claim 1,
wherein the radiation protection curtain has a first curtain part and a second curtain part, the first curtain part and the second curtain part being supported displaceably relative to one another along the bar-shaped area.

14. The computed tomography device as claimed in claim 13,
wherein the radiation protection curtain has a curtain part connection unit configured, in an area in which the first curtain part and the second curtain part overlap with one another while closing off a gap between the first curtain part and the second curtain part, to releasably connect the first curtain part and the second curtain part to one another and to counteract an opening of the gap.

15. The computed tomography device as claimed in claim 1,
wherein the radiation protection curtain has a first side flap connection unit, and
wherein, in a state in which the first side flap rests flat against the first central area of the radiation protection curtain, the first side flap connection unit is configured to releasably connect the first side flap and the first central area of the radiation protection curtain to one another and to counteract a folding up of the first side flap relative to the first central area of the radiation protection curtain about the first edge of the radiation protection curtain.

16. The computed tomography device as claimed in claim 1,
wherein the radiation protection curtain has an area transparent to visible light such that the examination object is visible through the radiation protection curtain when the examination object is located in the opening and when the curtain mounting is in the second position such that the radiation protection curtain covers the opening.

17. The computed tomography device as claimed in claim 1,
wherein the gantry has a first gantry part and a second gantry part,
wherein the first gantry part has a rotatably supported rotor with a projection data acquisition system,
wherein the second gantry part has at least one section of the opening,
wherein the curtain mounting is connected to the second gantry part via the pivot apparatus and is pivotably supported relative to the second gantry part about the pivot axis, and
wherein the first gantry part is configured to move relative to the second gantry part such that a translation movement of the first gantry part relative to the second gantry part is carried out, while at the same time the second gantry part remains still relative to the examination object and the radiation protection apparatus remains still relative to the examination object and relative to the at least one section of the opening when the examination object is located in the opening.

18. A method for radiation protection at a computed tomography device, wherein the computed tomography device has a gantry with an opening and a radiation protection apparatus configured to cover the opening, wherein the radiation protection apparatus has a radiation protection curtain, a curtain mounting and a pivot apparatus, wherein the curtain mounting has a bar-shaped area, wherein an upper edge of the radiation protection curtain is attached to the bar-shaped area such that the radiation protection curtain is stretched along the bar-shaped area and hangs down from the bar-shaped area, wherein, via the pivot apparatus, the curtain mounting is pivotably supported relative to the gantry about a pivot axis, and wherein the method comprises:
arranging the curtain mounting in a first position relative to the gantry, wherein the radiation protection curtain covers a side surface of the gantry and does not cover the opening when the curtain mounting is in the first position relative to the gantry;
introducing an examination object into the opening along a system axis of the gantry; and
moving, through a first pivoting movement, the curtain mounting about the pivot axis relative to the gantry from the first position to a second position, wherein
the radiation protection curtain covers the opening when the curtain mounting is in the second position,
the radiation protection curtain has a first side flap configured to be folded relative to a first central area of the radiation protection curtain about a first edge of the radiation protection curtain, and
the first edge of the radiation protection curtain is substantially perpendicular to the bar-shaped area.

* * * * *